(12) United States Patent
Mann et al.

(10) Patent No.: US 6,733,791 B2
(45) Date of Patent: May 11, 2004

(54) SUBLINGUAL COMPOSITIONS COMPRISING THYMOSIN FRACTION 5 AND METHODS FOR ADMINISTRATION THEREOF

(76) Inventors: Morris A. Mann, deceased, late of Glendale, AZ (US); Maria A. Mann, legal representative, 21669 N. 57th Ave., Glendale, AZ (US) 85308

( * ) Notice: Subject to any disclaimer, the term of this patent is extended or adjusted under 35 U.S.C. 154(b) by 0 days.

(21) Appl. No.: 10/192,684

(22) Filed: Jul. 8, 2002

(65) Prior Publication Data

US 2003/0031709 A1 Feb. 13, 2003

Related U.S. Application Data

(60) Provisional application No. 60/309,540, filed on Aug. 1, 2001.

(51) Int. Cl.[7] ............... A61K 35/26; A61K 35/12; A61K 35/28; A61K 38/00
(52) U.S. Cl. ............... 424/580; 424/435; 424/520; 424/562; 424/577; 424/578; 514/2; 514/12; 530/399; 530/837
(58) Field of Search ............... 424/562, 520, 424/435, 578, 577, 580, 439, 464, 465; 524/1, 12, 929; 930/180; 530/399, 837; 514/2, 21

Primary Examiner—Patricia Patten
(74) Attorney, Agent, or Firm—The Halvorson Law Firm

(57) ABSTRACT

Methods and compositions are described which allow for the sublingual absorption of peptides by oral administration. A liquid and a tablet format for the sublingual approach are demonstrated. The peptides are stable at room temperature and in the compositions herein described.

10 Claims, No Drawings

SUBLINGUAL COMPOSITIONS COMPRISING THYMOSIN FRACTION 5 AND METHODS FOR ADMINISTRATION THEREOF

This application claims the benefit of U.S. Provisional Application No. 60/309,540, filed on Aug. 1, 2001.

FIELD OF THE INVENTION

The present invention is generally directed to methods and compositions that allow for sublingual administration of peptides that are stable at room temperature. Said sublingual compositions are in liquid and sublingual tablet format.

BACKGROUND OF THE INVENTION

The ability to administer peptides orally and have them absorbed efficiently has been a long-standing problem. Peptides are very susceptible to acid hydrolysis in the gut. The hydrolysis of any given peptide typically eliminates its physiological efficacy.

Therefore, there exists a clear need in the art for methods and compositions that will facilitate the oral administration and absorption of peptides without subjecting them to acid hydrolysis.

The prior art discloses oral administration of peptides. However, these peptides travel to the gut for absorption by the stomach lining, thereby exposing the peptides to acid hydrolysis. The prior art also describes the sublingual administration of medicaments, such as vasodilating agents (these sublingual vasodilating agents are intended for systemic treatments such as heart problems and the like). However, the prior art does not disclose the sublingual absorption of peptides nor the use of vasodilators to assist in the sublingual absorption of vasodilators.

SUMMARY OF THE INVENTION

It is an object of the present invention to provide new and improved methods and compositions for the oral delivery of peptides to animals, preferably warm-blooded mammals, such as humans, pets and the like. The compositions provided herein may be produced in both tablet and liquid forms and are administered sublingually. The compositions comprise a room temperature stable peptide or complex of peptides that may be administered in a dosage of between 0.0001 mg/ml or gm and 600 mg/ml or gm.

It is another object of the present invention to provide a liquid composition that comprises a given peptide mixed in a mostly anhydrous medium, preferably comprising glycerin, a non-volatile water soluble solvent such as propylene glycol or one of the polyethylene glycols, and a topically effective vasodilator. The vasodilator can be methyl nicotinate, khellin, nitroglycerin, a calcium antagonist such as nifedipine, and the like. The addition of a different vasodilator, other than those noted above, does not change or alter the spirit of the invention. A surfactant, such as polysorbate 20, 60, or 80, may also be added to enhance absorption. Clearly, many other surfactants may be used in varying concentration without altering the spirit of the invention.

In the solid or liquid sublingual composition, a given peptide is mixed with an appropriate non-volatile water soluble solvent and a solid yet water soluble carrier such as lactose, sucrose, mannitol, and the like. Many other carriers and solvents can be used without altering the spirit of the invention. Solvents include, but are not limited to, propylene glycol, the polyethylene glycols, and the like. In addition, an appropriate vasodilator is added to the composition so as to increase vascular activity and thereby absorption by the sublingual mucous membranes of warm blooded mammals. As noted above, a surfactant, such as polysorbate 20, 60, or 80, may be used to enhance absorption. Clearly, many other surfactants may be used in varying concentration without altering the spirit of the invention.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DESCRIPTION OF THE PREFERRED EMBODIMENTS

The present invention is a composition for the sublingual application of medicaments and the like, and methods thereof.

A liquid preparation containing a peptide with enhanced properties for the absorption of the sublingual mucosa of a warm-blooded mammal can be made a variety of different ways. Although many specific details associated with certain aspects of the invention are set forth below, those skilled in the art of pharmaceutical manufacture and specifically those skilled in the art of drug delivery will recognize that the present invention may have additional embodiments or that the invention may be practiced without several of the details disclosed herein.

A representative liquid formulation can be described utilizing thymosin fraction 5 as the peptide. Thymosin fraction 5 is a complex of thymic peptides that is stable at room temperature. The individual component peptides each have a molecular weight of less then 20,000 daltons.

EXAMPLE I

|   | gm/% | Range % |
|---|---|---|
| 1. Thymic Fraction 5 | 5.0 | 0.001–55 |
| 2. Glycerin | 44.5 | 0.001–99 |
| 3. Propylene glycol | 44.9 | 0.001–99 |
| 4. Methyl nicotinate | 0.1 | 0.00001–25 |
| 5. Water | 50 | 0–99 |
| 6. Polysorbate 80 | 0.5 | 0.0001–25 |

This composition may then be administered to a warm-blooded mammal until the desired dosage is achieved. The methyl nicotinate, by increasing local (topical) blood flow, enhances absorption of the peptides contained in said composition.

Alternatively, a given peptide may be administered in a stable tablet formulation as a sublingual preparation to a warm-blooded mammal. A representative solid formulation administered sublingually in tablet form can be described utilizing thymosin fraction 5 as the peptide. As noted previously, thymosin fraction 5 is a complex of peptides that is stable at room temperature. The individual component peptides each have a molecular weight of less than 20,000 daltons.

EXAMPLE 2

|   | gm/% | Range % |
|---|---|---|
| 1. Thymosin fraction 5 | 5.0 | 0.0001–70 |
| 2. Water | 5.0 | 0–25 |
| 3. Sucrose/Lactose | 69.5 | 25–99 |
| 4. Propylene glycol | 0.5 | 0.0001–50 |
| 5. Silicon Dioxide | 15.0 | 0–70 |
| 6. Methyl nicotinate | 0.5 | 0.00001–25 |

The wetted mixture is formed into tablets of a desired weight. Said tablets are then dried at 30° C. for 36 hrs.

In use, the liquid composition or tablet composition is administered under the tongue of a warm-blooded mammal at the appropriately desired dosage.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A solid composition for sublingual application comprising:
   a) thymosin fraction 5,
   b) sucrose and/or lactose,
   c) Propylene Glycol, and
   d) Methyl nicotinate.

2. The composition of claim 1 further comprising a surfactant.

3. The composition of claim 2 wherein the thymosin fraction 5 is generally 5% by weight of the composition, the sucrose and/or lactose is 44.5% by weight of the composition;
   the Propylene Glycol is 44.9% by weight of the composition, and the Methyl nicotinate is 0.1% by weight of the composition.

4. The composition of claim 3 further comprising a surfactant that is 0.5% by weight of the composition.

5. The composition of claim 4 in tablet form.

6. The composition of claim 3 in tablet form.

7. The composition of claim 1 wherein the thymosin fraction 5 ranges from 0.001 to 99% by weight of the composition, the sucrose and/or lactose ranges from 0.001 to 99% by weight of the composition, the Propylene Glycol ranges from 0.001 to 99% by weight of the composition, and the Methyl nicotinate ranges from 0.00001 to 25% by weight of the composition.

8. The composition of claim 1 further comprising a surfactant that ranges from 0.0001 to 25% by weight of the composition.

9. A method for administering a solid medicament comprising the steps of:
   a) providing a solid composition comprising thymosin, fraction 5 Propylene Glycol, sucrose and/or lactose, and Methyl nicotinate;
   b) placing the composition under the tongue of an animal; and
   c) allowing the composition to be sublingually absorbed by the animal.

10. The method according to claim 9 wherein the composition further includes a surfactant.

* * * * *